United States Patent [19]

Schmid et al.

[11] 4,078,137

[45] Mar. 7, 1978

[54] PROCESS FOR MANUFACTURING A FLAVONE DERIVATIVE

[75] Inventors: Christian Schmid, Adlsiwil; Max Glasbrenner, Zurich; Jean Heusser, Langnau, all of Switzerland

[73] Assignee: Hommel Aktiengesellschaft, Adliswil, Switzerland

[21] Appl. No.: 683,790

[22] Filed: May 6, 1976

[30] Foreign Application Priority Data

May 16, 1975 Switzerland .................. 6335/75

[51] Int. Cl.$^2$ .......................................... C07H 15/00
[52] U.S. Cl. ................................................... 536/8
[58] Field of Search .................................. 536/8, 122

[56] References Cited

U.S. PATENT DOCUMENTS

| 3,661,890 | 5/1972 | Jurd | 536/8 |
| 3,751,570 | 8/1973 | Leroi | 536/8 |

FOREIGN PATENT DOCUMENTS

| 959,407 | 6/1964 | United Kingdom | 536/8 |

OTHER PUBLICATIONS

"Chem. Ber." vol. 33, pp. 326–327, 1900.
Mitchell, "Chem. Abst." vol. 74, 1971, pp. 130, 372.

*Primary Examiner*—Johnnie R. Brown
*Attorney, Agent, or Firm*—Werner W. Kleeman

[57] ABSTRACT

A process for manufacturing pure diosmin suitable as a therapeutic agent comprising acetylating hesperidin, observing by means of ultraviolet absorption the progress of the acetylation reaction and continuing such reaction until there disappears the band initially occurring at a wave length in the range of 264 to 280 nm and there appears in place thereof a new maximum at a wave length of about 330 nm. Thereafter the acetylation product is brominated, the obtained bromination product hydrolyzed and the obtained product after precipitation isolated, in order to obtain diosmin having a bromine content less than 0.1%.

8 Claims, No Drawings

PROCESS FOR MANUFACTURING A FLAVONE DERIVATIVE

BACKGROUND OF THE INVENTION

The present invention relates to a new and improved process for manufacturing pure diosmin (5,7,3'-trihydroxy-4'-methoxyflavone-7-rhamnoglucoside, molecular formula: $C_{28}H_{32}O_{15}$) suitable as a therapeutic agent. The process is a semi-synthetic process which starts from hesperidin obtained as a natural product.

Diosmin is a natural bioflavonoid which, for instance, can be found in citrus fruits. Its use as a tonic agent for veins or as a liver protective agent is well known.

Publications heretofore described a number of techniques for obtaining diosmin from hesperidin. The authors of such works manufactured the diosmin in small quantities in order to obtain proof of the structure of the naturally obtained diosmin. The diosmin manufactured in accordance with the process described in the prior art publications is generally only obtained with small yield and purity. A method for manufacturing diosmin on an industrial scale for using the flavonoid as a therapeutic agent has not heretofore been described.

SUMMARY OF THE INVENTION

Hence, it is a primary object of the present invention to devise a new and improved process which —in contrast to the already known methods— renders possible both an economical fabrication of the product as well as also obtaining sufficient purity to allow for therapeutic applications.

The economies of manufacture are predicated upon the costs of the pure natural product which is relatively expensive to obtain from plants. The purity of the preparation is predominantly impaired due to the presence of bromine derivatives in the final product.

The diosmin which is produced according to the publicized methods is always contaminated with different by-products, for instance hesperidin, and contains 1 to 2% by weight of bound bromine. It is obvious that diosmin which is thus contaminated cannot be used for therapeutic applications since it exhibits damaging properties as has been demonstrated during chronic toxicity tests with animals.

Now in order to implement the above objects, and others which will become more readily apparent as the description proceeds, the process of the invention is manifested by the features that there is acetylated hesperidin, the process of the acetylation reaction is observed by means of ultraviolet-absorption and continued for such length of time until the band initially appearing in the wave length range of 264 nm to 280 nm disappears and in place thereof there appears a new maximum at a wave length of 330 nm. Thereafter there is brominated the acetylation product, the obtained bromination product is hydrolyzed and the obtained product after once precipitating is isolated in order to obtain diosmin having a bromine content of less than 0.1% by weight.

In this manner there is realized a significant increase in the raw yield of the diosmin. It amounts to 65% to 80% of the theoretical amount, whereas with the heretofore known methods there could only be obtained a yield in the order of about 40% of the theoretical amount as has been disclosed in publications. This is especially of significance because the process of the invention requires a considerably less expenditure in work, material and energy, so that there can be realized economies which were not heretofore possible.

Additionally, it is possible with the process of the invention to reduce the bromine content of the end product to less than 0.1% by weight, whereas the products obtained with the heretofore known techniques had a bromine content in the order of 1% to 2% by weight. Due to the low bromine content which can be obtained with the invention it is only thus possible to even be able to use the product for therapeutic purposes.

In order to obtain a final end product which is almost free of bromine it is important to carry out with great care the protective acetylation and to exactly follow the indicated conditions.

A further advantage of the process of the invention is that the high degree of purity and the exceptional yield not only can be realized in the laboratory but also with the operating conditions on a technical scale.

The following authors have previously been involved for scientific reasons (investigation of the structures) with the production of diosmin from hesperidin:

Diosmin was first described by O. A. Osterle and G. Wander, Helv. Chim. Acta, 8, 519 to 536 (1925).

Already prior thereto Kostanecki et al, Ber. 32, 326 (1899); Ber. 33, 326 (1900); Ber. 37, 2634 (1904) converted flavanones by brominization in carbon disulfide and by fission from hydrogen bromide by means of alcoholic potassium hydroxide solution into flavone.

G. Zemplen and R. Bognar, Ber. 76, 452 (1943) brominated hesperidin acetate in chloroform with ultraviolet radiation and dehydrobrominated and deacetylated such by means of alcoholic lye. Their yield of diosmin amounted to 37%.

N. Narasimhachari and T. R. Seshadri, Proc. Indian Acad. Sci., 30 A, 151 to 62 (1949) produced flavones by dehydration with iodine and sodium acetate in an alcoholic solution of the flavanones. The yield in diosmin was not given.

N. B. Lorette et al, as described in J. Org. Chem. 16, 930 to 933 (1951) first used N-bromosuccinimide and pyridinium bromideperbromide for the bromination of hesperidin acetate in chloroform with benzoyl peroxide as the catalyst. Their yield amounted to 44% related to the employed hesperidin acetate.

For comparison purposes with natural diosmin, R. M. Horowitz, as described in J. Org. Chem, 21, 1184 to 1185 (1956) synthesized it from hesperidin according to N. B. Lorette and commented as follows:

"Although the method is easy to carry out, the yield is low and the diosmin contains a small quantity of a bromo derivative".

In order to prove the presence of diosmin in galium mollugo lin., J. Polonia and M. A. Polonia, as described in Anais da Faculdade de Farmacia do Porto, 27, 1 to 22 (1967) likewise worked according to the teaching of N. B. Lorette and obtained from hesperidin a yield of 39.6% diosmin.

DETAILED DESCRIPTION OF THE INVENTION

In order to further explain the invention there will now be given several examples:

EXAMPLE 1

A mixture of 72 grams hesperidin, 288 ml acetic anhydride and 300 ml glacial acetic acid were boiled in reflux with 15 ml pyridine as the catalyst for 144 hours, until during the control of the reaction the band disappeared at a wave length between 264 to 280 nm, and a new maximum appeared at 330 nm. Thereafter in a rotation evaporator the reaction mixture was concentrated by evaporation under vacuum conditions.

The residue was absorbed in 1200 ml ethyl acetate, admixed with 20 ml ethanol and boiled for one hour under reflux action. The solution was filtered and compressed to dryness. The residue was dried in a vacuum drying cabinet. The yield amounted to 107.5 grams.

35.8 grams thereof were then dissolved in 280 ml glacial acetic acid and brominated with a solution of 6.05 grams bromine in 30 ml glacial acetic acid. Thereafter the mixture compressed to dryness by means of the rotation evaporator, there being obtained a residue of 41.8 grams. Such was dissolved in 150 ml methanol, admixed with a solution of 36 grams sodium hydroxide in 180 ml water and stirred for one hour at 50° C.

The diosmin was precipitated out by adding 120 ml glacial acetic acid and stirring at 70° C for 30 minutes. The precipitate was filtrated in a suction filter or strainer, washed with methanol, water and again methanol and dried at 60° C in the drying cabinet. Raw yield: 17.0 grams corresponding to 71% yield. Bromine content 0.51%.

10 grams of the thus obtained diosmin was dissolved in a solution of 24 grams sodium hydroxide in 120 ml water, admixed with 100 ml methanol and 100 ml pyridine and stirred for one hour at 50° C. The diosmin was precipitated by the addition of 100 ml glacial acetic acid and stirred for 30 minutes at 70° C, filtered and washed with methanol and water and again methanol. After drying at 60° C there was obtained a pure yield of 9.2 grams diosmin (65% based upon the employed hesperidin) having a bromine content of 0.07%.

EXAMPLE 2

A mixture of 72 grams hesperidin, 288 ml acetic anhydride and 300 ml glacial acetic acid were boiled in reflux with 150 ml pyridine as the catalyst, until during the control with the spectrophotometer the band disappeared at 264 to 280 nm and a new maximum appeared at 330 nm, this occurring after 86 hours. Then, the mixture was vaporized in order to dry it in the rotation evaporator, the residue dissolved in 1000 ml ethyl acetate and after the addition of 20 ml ethanol boiled in reflux for two hours. After filtration the ethyl acetate was distilled off and the residue dried in a vacuum drying cabinet. The yield amounted to 105.5 grams.

25 grams of this acetylated-intermediate product was dissolved in 200 ml ethyl acetate and brominated with a solution of 4.35 grams bromine in 50 ml ethyl acetate. The obtained solution was evaporated to dryness, the residue dissolved in 100 ml methanol and admixed with a solution of 25 grams sodium hydroxide in 130 ml water. After stirring for one hour at 50° C there was added 100 ml glacial acetic acid and the mixture heated to 70° C in order to precipitate the diosmin. After the suction filtering and washing, as described in conjunction with Example 1, and drying at 60° C, there was obtained a raw yield of 11.6 grams corresponding to 68.2%. The purification was carried out in the manner of Example 1.

EXAMPLE 3

A mixture of 72 grams hesperidin, 300 ml acetic anhydride and 150 ml glacial acetic acid were boiled in reflux with 75 ml pyridine as the catalyst, until during the control with the spectrophotometer there was observed the disappearance of the band at 264 to 280 nm and the occurrence of a new maximum at 330 nm, indicating the complete reaction, which occurred after 23 hours.

The solution was then divided into three parts and one part was evaportated to dryness. The residue was absorbed in 150 ml ethylene chloride and brominated with a solution of 6.7 grams bromine in 50 ml ethylene chloride. Then there were added 100 ml methanol and 200 ml of a mixture of concentrated sodium hydroxide solution- water (mixing ratio 1:1) and stirred for 30 minutes at 45° C. Thereafter the pH was adjusted to 5.6 by means of glacial acetic acid, heated to 70° C and stirred at this temperature for 30 minutes. Then the mixture was suction filtered and washed with methanol, water and again methanol. After drying at 60° C there was obtained a raw yield of 16.0 grams diosmin corresponding to 67% of the theoretical amount (calculated based upon the employed hesperidin).

Purification was undertaken in the manner described in conjunction with Example 1.

EXAMPLE 4

A mixture of 24 grams hesperidin, 100 ml glacial acetic acid and 340 ml acetic acid anhydride together with 16 grams crystallized sodium acetate were boiled in reflux, until during the control with the spectrophotometer there occurred the disappearance of the band at 264 to 280 nm and the occurrence of a new maximum at 330 nm, indicating the complete reaction, which occurred after 21 hours. The mixture was evaporated in vacuum to dryness and the residue boiled with 100 ml ethylene chloride. The undissolved sodium acetate was filtered off and brominated directly in the solution with 6.05 grams bromine (dissolved in 50 ml ethylene chloride). Then there were added 160 ml methanol, 100 ml concentrated sodium hydroxide solution and 100 ml water and stirred for 45 minutes at 50° C. Thereafter in a separating funnel there was separated out the ethylene chloride. The aqueous layer was freed from the methanol by distillation and admixed with 160 ml pyridine. By means of acetic acid, by adjusting the pH to 5.8, there was precipitated out the diosmin.

The obtained suspension was stirred for 30 minutes at 70° C and suction filtered after cooling. After washing with methanol and water and again methanol and drying at 60° C there was obtained 15.7 grams raw diosmin corresponding to 65.5% of the theoretical amount and having a bromine content of 0.22%.

By precipitating 10 grams of the thus obtained diosmin by dissolving in 50 ml of a 10% sodium hydroxide solution, adding 50 ml pyridine, stirring for 1 hour at 50° C, precipitating with glacial acetic acid and washing with methanol and water and drying at 60° C, there was obtained 9.8 grams of pure diosmin (64% yield) having a bromine content of 0.063%.

EXAMPLE 5

48 grams hesperidin, 320 grams acetic acid anhydride and 6 grams potassium acetate were boiled in reflux until, as described in Examples 1 to 4, there could be ascertained the complete reaction, which occurred after 5 hours. Due to the removal of a sample the total weight of the preparation was reduced to 355.5 grams. Of such 177.7 grams were evaporated to dryness in a rotation evaporator and then boiled with 250 ml ethylene chloride until complete solution. This solution, without previously removing the potassium acetate, was brominated with 6.05 grams bromine in 50 ml ethylene chloride. Then there were added 160 ml methanol and 200 ml of a mixture of concentrated sodium hydroxide solution/water (mixing ratio 1:1) and stirred for one hour at 50° C. In a separation funnel there was thereafter separated out the ethylene chloride, the aqueous solution admixed with 160 ml pyridine and with glacial acetic acid the pH adjusted to 7. For precipitation the mixture was heated to 70° C and stirred for 30 minutes at this temperature. After cooling the diosmin was suction filtered, first washed with methanol/water (mixing ratio 1:1), then with water and finally with methanol and dried at 60° C. There was realized a yield of 18.0 grams raw diosmin corresponding to 79.3% of the theoretical amount. The bromine content amounted to 0.19%.

EXAMPLE 6

In a cast iron apparatus having an enamel lining 30 kg hesperidin together with 200 kg acetic anhydride and 21 kg crystalized sodium acetate as the catalyst were boiled in reflux for 17 hours. The control took place in the manner described in Examples 1 to 4. Then while continuously stirring the mixture was evaporated to dryness under vacuum. Thereafter 153 kg ethylene chloride were added and boiled in reflux for one hour. After cooling the sodium acetate was separated out in a centrifuge. The clear solution was again introduced into the enamel apparatus and brominated with 7.56 kg bromine, dissolved in 10 $l$ ethylene chloride. Thereafter there were added 100 $l$ methanol, 100 $l$ water and 90 $l$ concentrated sodium hydroxide solution and stirred for 1 hour at 50° C. Then the stirrer was stopped and the mixture cooled.

After 1 hour the layer of ethylene chloride was removed. After the distillation of the methanol from the aqueous solution there was added 107 $l$ pyridine and by means of glacial acetic acid there was adjusted a pH of 7.2. The thus obtained yield of diosmin was stirred for 30 minutes at 70° C and then cooled. The diosmin was thereafter freed from the mother liquor in a centrifuge.

The raw diosmin was dispersed in 60 $l$ methanol-water (mixing ratio 1:1) and again centrifuged. Thereafter the still moist diosmin was dissolved in a mixture of 30 $l$ concentrated sodium hydroxide solution, 83 $l$ water and 100 $l$ isopropyl alcohol and stirred for one hour at 50° C. Then with the aid of acetic acid, by adjusting the pH to 7, the pure diosmin was precipitated out, heated for 30 minutes to 70° C and after cooling centrifuged. The diosmin was initially dispersed in a mixture of 20 $l$ water and 60 $l$ methanol and centrifuged, then dispersed in 100 $l$ methanol, centrifuged and dried at 60° C. The pure yield of 18.8 kg diosmin corresponds to 63% of the theoretical amount, calculated on the basis of the employed hesperidin. The bromine content amounted to 0.09%.

Having now discussed in considerable detail illustrative and preferred embodiments of the invention, it should be apparent that the objects set forth at the outset of this specification have been satisfied. Accordingly,

What is claimed is:

1. In a method for manufacturing therapeutically pure diosmin having a bromine content of less than 0.1% by weight bromine which includes the steps of acetylating hesperidin, brominating the acetylated hesperidin, hydrolyzing the bromination product, precipitating the hydrolyzed product and isolating the precipitated product to obtain said diosmin, the improvement comprising:

carrying out and controlling the acetylation step in the presence of an effective acetylation catalyst until such time as the ultraviolet absorption band which initially appears at 264 to 280 nm disappears and a new maximum ultraviolet absorption band at about 330 nm appears.

2. The improvement according to claim 1 wherein the acetylation catalyst is pyridine.

3. The improvement according to claim 1 wherein the acetylation catalyst is sodium acetate.

4. The improvement according to claim 1 wherein the acetylation catalyst is potassium acetate.

5. The improvement according to claim 1 wherein the bromination step is carried out with ethyl acetate as a solvent.

6. The improvement according to claim 1 wherein the bromination step is carried out with ethylene chloride as a solvent.

7. The improvement according to claim 1 wherein the bromination step is carried out with glacial acetic acid as a solvent.

8. The improvement according to claim 1 wherein pyridine is added during the precipitation step.

* * * * *